US010441292B2

(12) United States Patent
Tsueda et al.

(10) Patent No.: US 10,441,292 B2
(45) Date of Patent: Oct. 15, 2019

(54) CLIP DEVICE FOR ENDOSCOPE

(71) Applicant: KANEKA CORPORATION, Osaka-shi, Osaka (JP)

(72) Inventors: Masato Tsueda, Okaya (JP); Yuki Mukai, Okaya (JP); Naotake Maekubo, Okaya (JP)

(73) Assignee: KANEKA CORPORATION, Osaka-Shi (JP)

( * ) Notice: Subject to any disclaimer, the term of this patent is extended or adjusted under 35 U.S.C. 154(b) by 127 days.

(21) Appl. No.: 15/516,144

(22) PCT Filed: Sep. 25, 2015

(86) PCT No.: PCT/JP2015/077211
§ 371 (c)(1),
(2) Date: Mar. 31, 2017

(87) PCT Pub. No.: WO2016/063679
PCT Pub. Date: Apr. 28, 2016

(65) Prior Publication Data
US 2017/0296197 A1 Oct. 19, 2017

(30) Foreign Application Priority Data

Oct. 24, 2014 (JP) .................................. 2014-217255

(51) Int. Cl.
*A61B 17/128* (2006.01)
*A61B 17/10* (2006.01)
(Continued)

(52) U.S. Cl.
CPC .......... *A61B 17/1285* (2013.01); *A61B 17/10* (2013.01); *A61B 17/122* (2013.01); *A61B 17/1227* (2013.01); *A61B 2017/00862* (2013.01)

(58) Field of Classification Search
CPC . A61B 17/1285; A61B 17/1227; A61B 17/10; A61B 17/122
(Continued)

(56) References Cited

U.S. PATENT DOCUMENTS 3,958,576 A * 5/1976 Komiya ............... A61B 17/083
606/142
5,304,183 A * 4/1994 Gourlay ........... A61B 17/00234
227/901

(Continued)

FOREIGN PATENT DOCUMENTS

JP 8-126648 A 5/1996
JP 2003-339718 A 12/2003
(Continued)

OTHER PUBLICATIONS

International Search Report issued in PCT/JP2015/077211 (PCT/ISA/210), dated Nov. 17, 2015.
(Continued)

*Primary Examiner* — Eric J Rosen
*Assistant Examiner* — Andrew P. Restaino
(74) *Attorney, Agent, or Firm* — Birch, Stewart, Kolasch & Birch, LLP

(57) ABSTRACT

A clip device for an endoscope of the present invention comprises an outer tubular body 70; an inner tubular body 80 provided in the outer tubular body 70; a line member 50 placed in the inner tubular body 80; and a pinching part 20, for holding an indwelling clip, connected to a distal side of the line member 50; wherein the pinching part 20 has two pinching base plates 30*a* and 30*b*, a blade part 40*a* is provided at a distal end of the pinching base plate 30*a* and formed toward an inside of the pitching base plate 30*a*, a blade part 40*b* is provided at a distal end of the pinching base plate 30*b* and formed toward an inside of the pinching base (Continued)

plate 30*b*, a Young's modulus of the blade part 40*a* is smaller than that of the pinching base plate 30*a*, and a Young's modulus of the blade part 40*b* is smaller than that of the pinching base plate 30*b*.

10 Claims, 6 Drawing Sheets

(51) Int. Cl.
*A61B 17/122* (2006.01)
*A61B 17/00* (2006.01)

(58) Field of Classification Search
USPC .......................................................... 606/142
See application file for complete search history.

(56) References Cited

U.S. PATENT DOCUMENTS

| | | | | |
|---|---|---|---|---|
| 5,415,666 | A | * | 5/1995 | Gourlay ............ A61B 17/00234 606/139 |
| 5,766,184 | A | | 6/1998 | Matsuno et al. |
| 2003/0069592 | A1 | * | 4/2003 | Adams ................. A61B 17/122 606/142 |
| 2005/0080440 | A1 | * | 4/2005 | Durgin ................. A61B 17/122 606/157 |
| 2006/0259049 | A1 | * | 11/2006 | Harada ................. A61B 17/122 606/151 |
| 2008/0255427 | A1 | * | 10/2008 | Satake ................... A61B 17/08 600/204 |
| 2009/0275958 | A1 | | 11/2009 | Harada et al. |
| 2010/0331674 | A1 | * | 12/2010 | Sohn .................. A61B 17/1227 600/431 |
| 2011/0238093 | A1 | * | 9/2011 | Matsuoka .......... A61B 17/1285 606/151 |
| 2013/0253275 | A1 | * | 9/2013 | Ransden ............ A61B 17/0218 600/204 |
| 2014/0171973 | A1 | * | 6/2014 | Zhu ...................... A61B 17/122 606/144 |

FOREIGN PATENT DOCUMENTS

| | | |
|---|---|---|
| JP | 2005-58627 A | 3/2005 |
| JP | 2007-283080 A | 11/2007 |
| JP | 2011-78592 A | 4/2011 |
| JP | 2014-18509 A | 2/2014 |
| WO | WO 2004/082488 A1 | 9/2004 |

OTHER PUBLICATIONS

Written Opinion of the International Searching Authority issued in PCT/JP2015/077211 (PCT/ISA/237), dated Nov. 17, 2015.

* cited by examiner

[Fig. 1]
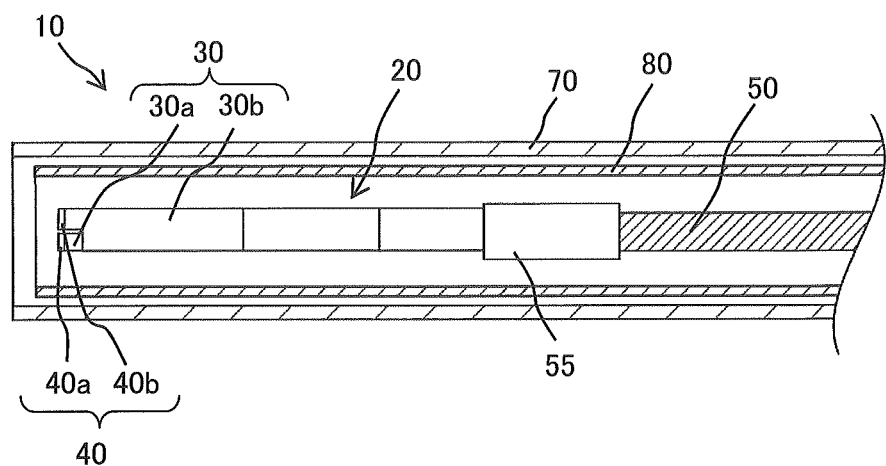
[Fig. 2]
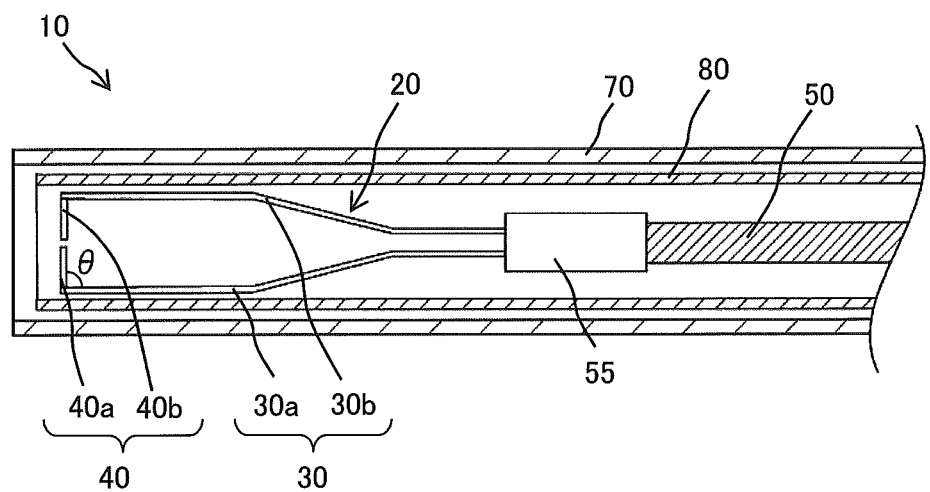

[Fig. 3A]
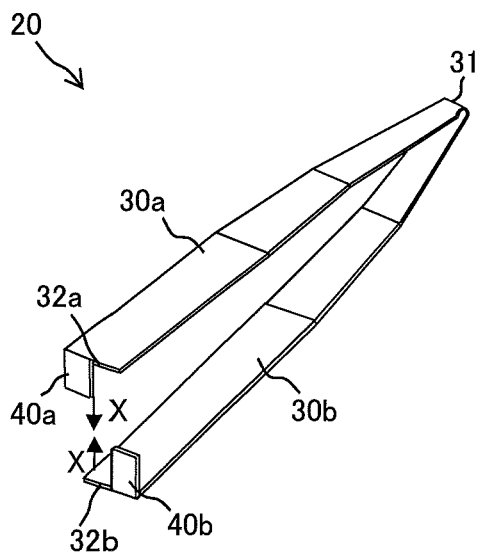
[Fig. 3B]
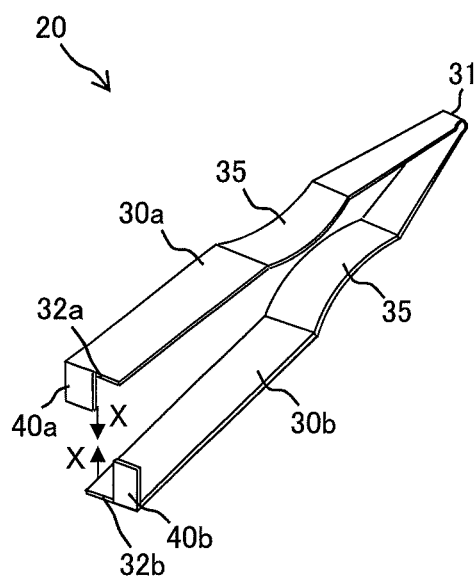

[Fig. 4A]
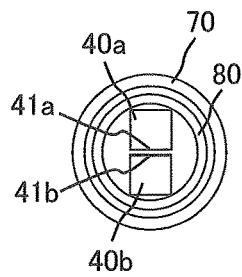
[Fig. 4B]
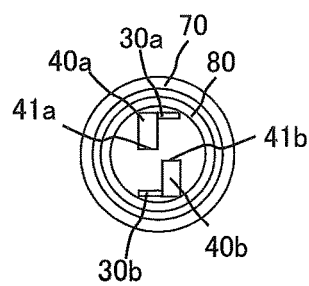
[Fig. 4C]
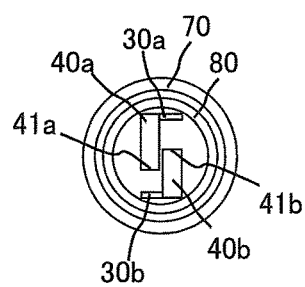
[Fig. 4D]
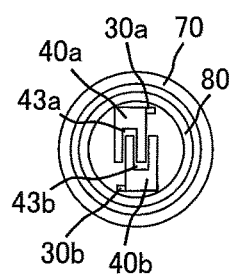

[Fig. 5]
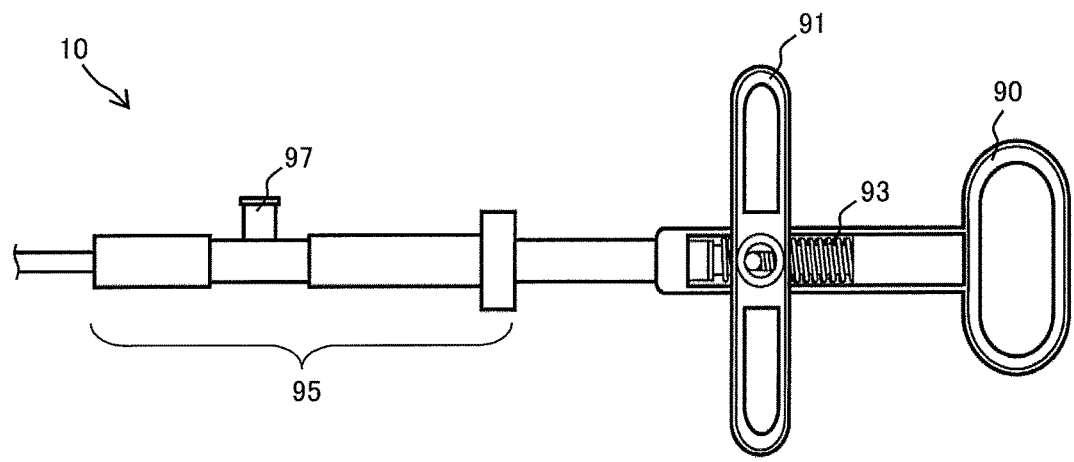
[Fig. 6]
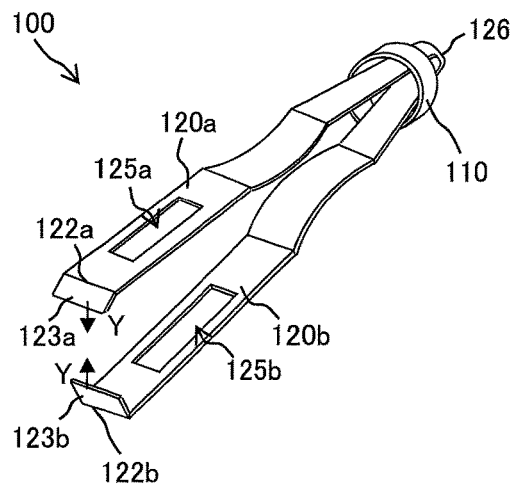

[Fig. 7]
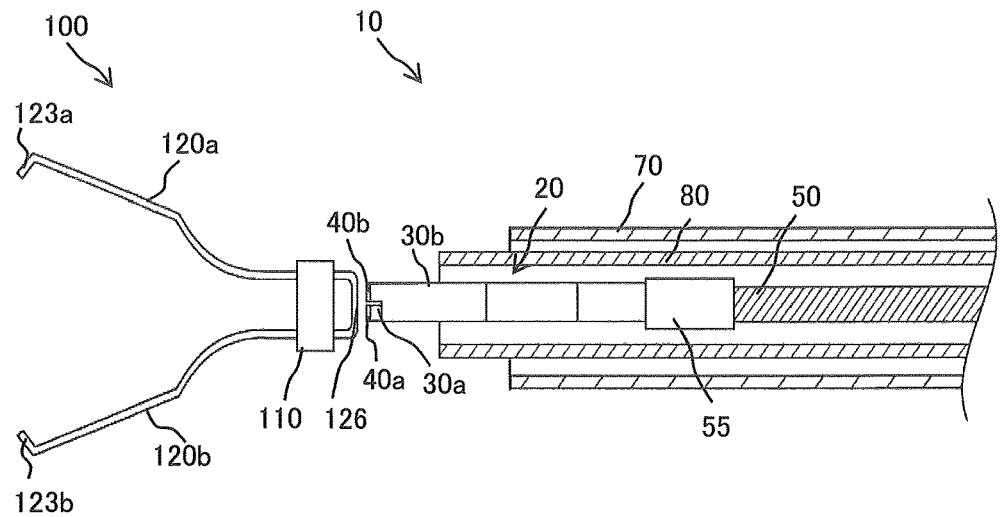
[Fig. 8]
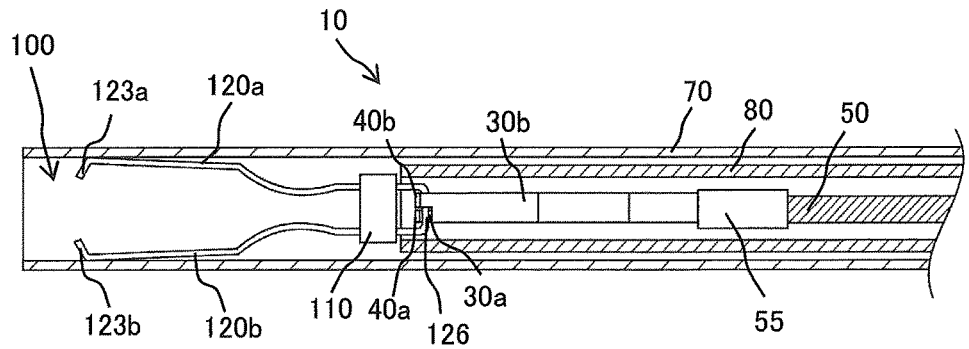
[Fig. 9]
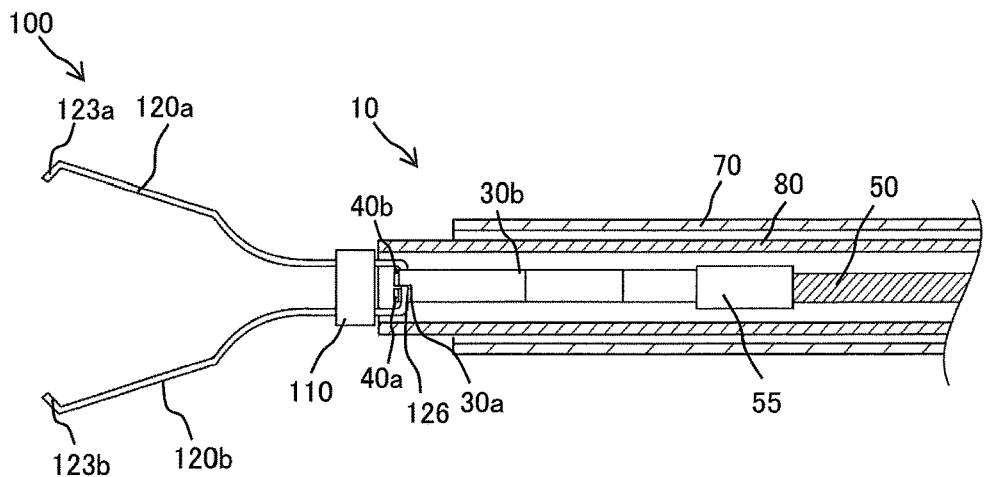

[Fig. 10]
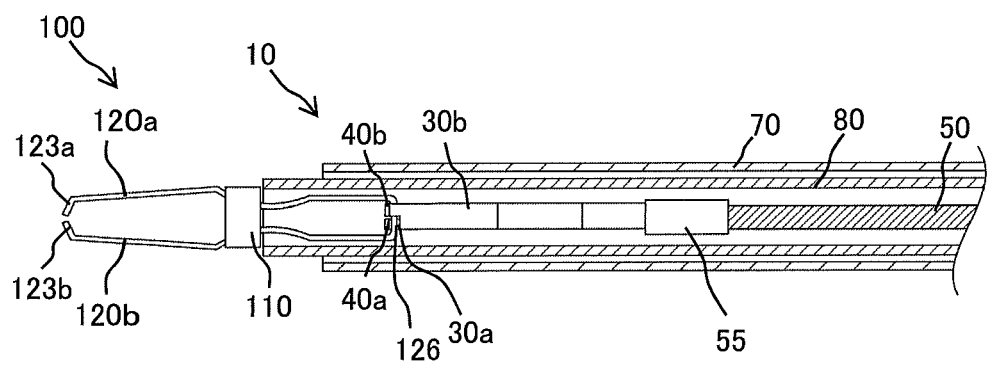
[Fig. 11]
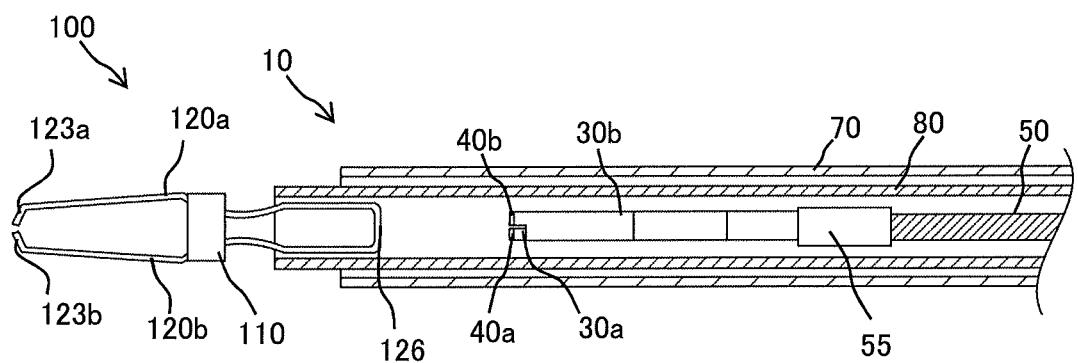

CLIP DEVICE FOR ENDOSCOPE

TECHNICAL FIELD

The present invention relates to a clip device for endoscope for holding and placing an indwelling clip.

The present invention also relates to a method for installing an indwelling clip with a clip device for an endoscope.

BACKGROUND ART

Recently endoscopic submucosal dissection (ESD) and endoscopic mucosal resection (EMR) have been adopted for early-stage cancer surgery with an endoscope. Since ESD and EMR enable an excision of a relatively large lesion, the postsurgical recurrence of disease tends to be low, however, bleeding and perforation may occur due to the incision. In early stage cancer surgery, an indwelling clip is used for holding a tissue in a body to prevent bleeding and lower the risk of tissue crush. Various clip devices for holding and placing an indwelling clip have been developed.

Patent Literature 1 discloses a clip device including a means for preventing a connection member extending from the back of a clip and connected to a traction member, from entering a tip part of a sheath beyond a predetermined range.

Patent Literature 2 discloses a clip device for gripping a tissue in a body, including: an outer tube to be inserted into a body cavity, an operating member slidably inserted into the outer tube, an operating wire slidably inserted into the operating member, a self-opening griping member disposed on the tip end of the operating wire and configured to open and close due to the back and forth movement of the operating member, and a self-opening clip having a griping part attached to or removed from the tip of the gripping member due to the opening or closing of the gripping member and configured to grip a tissue in a body.

CITATION LIST

Patent Literature
Patent Literature 1
    Japanese Unexamined Patent Application Publication No. 2003-339718
Patent Literature 2
    WO 2004/082488

SUMMARY OF INVENTION

Technical Problem

In the clip device of Patent Literature 1 or 2, the traction member or the operating wire needs to be pushed forward for releasing the clip from the traction member or the gripping member to place the clip in a body before being pulled back, which complicates the release of the clip from the clip device.

An object of the present invention is to provide a clip device for an endoscope that enables easy release of an indwelling clip.

Another object of the present invention is to provide a method for installing an indwelling clip that enables easy release of an indwelling clip from a clip device for an endoscope.

Solution to Problem

A clip device for an endoscope of the present invention which is able to achieve the above object comprises an outer tubular body; an inner tubular body provided in the outer tubular body; a line member placed in the inner tubular body, and a pinching part, for holding an indwelling clip, connected to a distal side of the line member; wherein the pinching part has two pinching base plates, a blade part is provided at a distal end of the pinching base plate and formed toward an inside of the pinching base plate, and a Young's modulus of the blade part is smaller than that of the pinching base plate. In the clip device for an endoscope of the present invention, the blade part is easy to be elastically deformed due to its small Young's modulus, which enables easy release of the indwelling clip from the clip device for an endoscope when a tensile load is applied to a pinching part holding the indwelling clip in the direction away from the indwelling clip.

A clip device for an endoscope of the present invention also comprises an outer tubular body, an inner tubular body provided in the outer tubular body; a line member placed in the inner tubular body; and a pinching part, for holding an indwelling clip, connected to a distal side of the line member; wherein the pinching part has two pinching base plates, a blade part is provided at a distal end of the pinching base plate and formed toward an inside of the pinching base plate, and a width of the blade part is smaller than that of the pinching base plate. In the clip device for an endoscope of the present invention, the blade part has a small width, which reduces a necessary tensile load to be applied to the blade part for releasing the indwelling clip from the clip device for an endoscope.

In the clip device for an endoscope, it is preferred that the blade part provided on a tip of one of the pinching base plates and the blade part provided on a tip of the other of the pinching base plates are alternately arranged. The alternate arrangement of the blade parts enables the pinching part to easily continue to hold the clip, which prevents the indwelling clip from falling off the clip device for an endoscope.

In the clip device for an endoscope, an angle of the blade part to the pinching base plate is preferably larger than 90° and smaller than 180° to securely hold the indwelling clip by the pinching part.

In the clip device for an endoscope, the pinching base plate and the blade part are preferably integrally formed. The integral forming eliminates the necessity for joining the pinching base plate and the blade part by mechanical securing such as using screws or caulking, welding, or bonding, which simplifies the manufacturing process of the pinching part.

In the clip device for an endoscope, the blade part is composed of a Ni—Ti alloy or a stainless steel. A Ni—Ti alloy has not only excellent strength, biocompatibility and corrosion resistance, but also super elasticity and excellent shape recovery properties. The clip device for an endoscope thus easily recovers the original shape even if the attachment and removal of the clip are repeated. A stainless steel also has excellent biocompatibility and corrosion resistance.

The indwelling clip used in the clip device for an endoscope preferably comprises a fastener member having an outer diameter larger than an inner diameter of the inner tubular body and being movable in the axial direction. When the pinching part is pulled toward the proximal side into the inner tubular body during an operation, the fastener member is caught on the distal end of the inner tubular body which prevents the indwelling clip from entering the inner tubular body.

The present invention includes the clip device for an endoscope further comprising a first handle connected to a proximal side of the inner tubular body and being movable in the axial direction with respect to the outer tubular body, and a second handle connected to a proximal side of the line member and being movable in the axial direction with respect to the outer tubular body. These handles facilitate the moving operation of the inner tubular body and the line member.

In the clip device for an endoscope, a length of the blade part is preferably not more than half of an inner diameter of the inner tubular body. This reduces a necessary tensile load to be applied in the blade part for releasing the indwelling clip from the clip device for an endoscope.

In the clip device for an endoscope, a thickness of the blade part is preferably smaller than that of the pinching base plate. The smaller thickness of the blade part makes the blade part easier to be deformed, which enables easy release of the indwelling clip from the clip device for an endoscope.

In the clip device for an endoscopes the pinching base plate preferably has a curved part which is curved toward an inside of the pinching part in at least a part of the pinching base plate. The curved part in the pinching base plate enables the pinching base plate to easily bend and enables the distal side of the pinching part to expand outward, which makes it easy to hold the indwelling clip with the pinching part.

The present invention further provides a method for installing an indwelling clip with a clip device for an endoscope, in which the clip device for endoscope comprises an outer tubular body, an inner tubular body provided in the outer tubular body, a line member placed in the inner tubular body, and a pinching part, for holding an indwelling clip, connected to a distal side of the line member, wherein the pinching part has two pinching base plates, and a blade part is provided at a distal end of pinching bass plate and formed toward an inside of the pinching base plate, comprising the steps of holding a target site with the indwelling clip; and pulling the line member toward a proximal end side without pushing the line member toward the distal end side with respect to the inner tubular body, whereby the indwelling clip rides over the blade part and the indwelling clip is released from the pinching part.

In the present invention, the method for installing an indwelling clip does not involve pushing the pinching part toward the distal end side with respect to the inner tubular body for placing the indwelling clip after holding a target site such as a lesion with the indwelling clip, which enables easy release of the indwelling clip front the pinching part.

Advantageous Effects of the Invention

In the clip device for an endoscope of the present invention, the blade part is easy to be elastically deformed due to its small Young's modulus, which enables easy release of the indwelling clip from the clip device for an endoscope when a tensile load is applied to a pinching part holding the indwelling clip in the direction away from the indwelling clip.

Also, in the clip devise for an endoscope of the present invention, the blade part has a small width, which reduces a necessary tensile load to be applied to the blade part for releasing the indwelling clip from the clip device for an endoscope.

Further, in the present invention, the method for installing an indwelling clip does not involve pushing the pinching part toward the distal end side with respect to the inner tubular body for placing the indwelling clip after holding a target site such as a lesion with the indwelling clip, which enables easy release of the indwelling clip from the pinching part.

BRIEF DESCRIPTION OF THE DRAWINGS

FIG. 1 is a plan view (a partial cross-sectional view) of a distal side of a clip device for an endoscope according an embodiment of the present invention.

FIG. 2 is a side view (a partial cross-sectional view) of the distal side of the clip device for an endoscope according the embodiment.

FIG. 3A is a perspective view of the pinching part not provided with a curved part in a pinching base plate according to the embodiment, and FIG. 3B is a perspective view of the pinching part provided with a curved part in at least a part of the pinching base plate according to the embodiment.

FIGS. 4A to 4B are plan views of a distal side of a clip device for an endoscope according the embodiment seen from an axial direction; FIG. 4A shows that two blade parts have the almost same width as pinching base plates, and each length of the blade parts is not more than half of an inner diameter of an inner tubular body; FIG. 4B shows that the two blade parts have a width smaller than, that of the pinching base plates, and each length of the blade parts is not more than half of an inner diameter of an inner tubular body; FIG. 4C shows that two blade parts have a width smaller than that of pinching base plates, and each length of the blade parts is not less than half of an inner diameter of an inner tubular body; and FIG. 4D shows that a blade part has a cutout.

FIG. 5 is a plan view of a proximal side of the clip device for an endoscope according the embodiment.

FIG. 6 is a perspective view of an indwelling clip.

FIG. 7 is a plan view (a partial cross-sectional view) showing a movement of the clip device for an endoscope according the embodiment.

FIG. 8 is a plan view (a partial cross-sectional view) showing a movement of the clip device for an endoscope according the embodiment.

FIG. 9 is a plan view (a partial cross-sectional view) showing a movement of the clip device for an endoscope according the embodiment.

FIG. 10 is a plan view (a partial cross-sectional view) showing a movement of the clip device for an endoscope according the embodiment.

FIG. 11 is a plan view (a partial cross-sectional view) showing a movement of the clip device for an endoscope according the embodiment.

DESCRIPTION OF EMBODIMENTS

1. Clip Device for Endoscope

A clip device for an endoscope comprises an outer tubular body, an inner tubular body provided in the outer tubular body, a line member placed in the inner tubular body, and a pinching part, for holding an indwelling clip, connected to a distal side of the line member, wherein the pinching part has two pinching base plates, a blade part is provided at a distal end of the pinching base plate and formed toward an inside of the pinching base plate, and a Young's modulus of the blade part is smaller than that of the pinching base plate. In the clip device for an endoscopy of the present invention, the blade part is easy to be elastically deformed due to its small Young's modulus, which enables easy release of the indwelling clip from the clip device for an endoscope when a tensile load is applied to a pinching part holding the indwelling clip in the direction away from the indwelling clip.

The indwelling clip is used for pinching a tissue in a body for stopping bleeding, suturing, or marking under early-stage cancer surgery with an endoscope. In this description, the indwelling clip may simply be referred to as a "clip". More than ten clips may be used during one operation, depending on the type of operation. To shorten the surgical time to reduce the burden on a patient, the clips is preferably operated efficiently for holding a target site such as a lesion and released efficiently from the clip device for an endoscope described below.

The clip device for an endoscope is used for controlling the opening and closing of the above clip to hold a target site such as a lesion or to release the clip from the clip device for an endoscope after the holding process. In this description, the clip device for an endoscope may simply be referred to as a "clip device."

The present invention will be specifically explained below based on the following embodiments, however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

In the present invention, the axial direction refers to a long axis direction of the inner tubular body, and a proximal side in the axial direction refers to a direction of an operator's hand side, while a distal side refers to a direction opposite to the proximal side. Also, in the present invention, a radial direction refers to a radial direction of the inner tubular body, and an inner side in the radial direction refers to a direction toward a center of the inner tubular body, while an outer side refers to a radiation direction of the inner tubular body.

FIG. 1 is a plan view (a partial cross-sectional view) of a distal side of a clip device 10 for an endoscope according an embodiment of the present invention, and FIG. 2 is a side view (a partial cross-sectional view) of the distal side of the clip device 10 for an endoscope according the embodiment of the present invention. The clip device 10 for an endoscope comprises an outer tubular body 70, an inner tubular body 80 provided in the outer tubular body 70, a line member 50 placed in the inner tubular body 80, and a pinching part 20 for holding an indwelling clip 100, connected to a distal side of the line member 50.

The outer tubular body 70 places the inner tubular body 80 and an indwelling clip 100 in the lumen thereof and the inner tubular body 80 places the line member 50 and the pinching part 20 connected to the line member 50 in the lumen thereof. The outer tubular body 70 and the inner tubular body 80 protect a forceps opening of an endoscope, the inner wall of a forceps channel, and tissues in a body other than a target tissue, from being damaged by the clip 100 and the pinching part 20 while the indwelling clip 100 is being sent from the forceps opening of an endoscope through the forceps channel to the target tissue in a patient.

The inner tubular body 80 preferably has balanced combination of flexibility to bend along the shape of a body cavity and rigidity to reach a target tissue. The inner tubular body 80 may be made of a coiled metal member, a plurality of short cylindrical joint pieces rotatably connected in the axial direction, or a synthetic resin such as polytetrafluoroethylene (PTFE), and is preferably made of a high-strength metal coil or a high-strength synthetic resin.

The outer tubular body 70 is more preferably made of a synthetic resin such as PTFE and polypropylene to improve the flexibility to bend along the movement of a curved tube of an endoscope.

The line member 50 is connected to the proximal end 31 of the pinching part 20 on the distal side to move the pinching part 20 back and forth in the axial direction. To prevent the pinching part 20 from falling off the line member 50, the line member 50 is connected to the pinching part 20 by mechanical securing including using a connecting member 50 such as a screw or caulking, welding, or bonding. The line member 50 preferably has flexibility like the outer tubular body 70 and the inner tabular body 80, and may be made of a metal wire such as a stainless steel wire and a carbon steel wire, or plastic fibers such as polyamide, polyester, and polyethylene.

FIG. 3A is a perspective view of the pinching part 20 not provided with a curved part 35 in each of pinching base plates 30a and 30b according to the embodiment, and FIG. 3B is a perspective view of the pinching part 20 provided with a curved part 35 in at least a part of each of the pinching base plates 30a and 30b. The pinching part 20 holds the indwelling clip 100. As shown in FIGS. 3A and 3B, the pinching part 20 includes two pinching base plates 30a and 30b close to each other on the proximal side. The blade part 40a formed toward an inside (X direction in FIG. 3) of the pinching base plate 30a is provided at a distal end 32a of the pinching base plate 30a, the blade part 40b formed toward an inside (the X direction in FIG. 3) of the pinching base plate 30b is provided at a distal end 32b of the pinching base plate 30b, and each proximal end 31 of the pinching base plates 30a and 30b is connected to the line member 50 by a connecting member 55.

As the line member 50 is pulled toward the proximal side, the pinching part 20 gradually closes along the inner shape of the inner tubular body 80. As the inner tubular body 80 applies pressing force to the pinching base plates 30a and 30b in the X direction, the blade parts 40a and 40b get close to each other until, the pinching part 20 holds the clip 100. As the line member 50 is pushed toward the distal side, the pinching part 20 is released from the inner tubular body 80 to expand outward. As the pressing force applied to the pinching base plates 30a and 80b in the X direction decreases, the blade parts 40a and 40b gradually separate from each other until the clip 100 is released from the pinching part 20 of the clip device 10.

The two pinching base plates 30a and 30b are close to each other on the proximal side. As shown in FIGS. 3A and 3B, the pinching base plates 30a and 30b may be formed by bending an integrally formed pinching base plate 30. Alternatively, the pinching base plates 30a and 80b may separately be made and then joined to each other by mechanical securing such as using screws or caulking, welding, or bonding (not shown).

As shown in FIG. 3A, the two pinching base plates 30a and 30b may symmetrically be formed in the axial direction. The two pinching base plates 30a and 30b approach to or separate from each other in the radial direction at the same timing, which enables easily holding of the clip 100 with the pinching part 20.

As shown in FIG. 3B, each of the pinching bass plates 30a and 30b may have a curved part 35 which is curved toward an inside (X direction) of the pinching part in at least a part. The curved part 35 in the pinching base plates 30a and 30b enables the pinching base plates 30a and 30b to easily bend and enables the distal side of the pinching part 20 to expand outward, which makes it easy to hold the indwelling clip 100. The part of the pinching base plate 30a means the region from the distal end 32a of the pinching base plate 30a to the proximal end 31, and the part of the pinching base plate 30b means the region from the distal end 32b of the pinching base plate 30b to the proximal end 31.

To shorten the time for one operation to reduce the physical burden on a patient, the operation is required to be done efficiently. The blade part 40 is preferably easy to be elastically deformed for easy release of the clip 100 from the pinching part 20. The pinching base plate 80 is preferably composed of a highly elastic metal material such as a stainless steel and a Ni—Ti alloy.

The blade part 40a is formed toward an inside (X direction in FIG. 3) of the pinching base plate 30a, the blade part 40b is formed toward an inside (the X direction in FIG. 3) of the pinching base plate 80b, a Young's modulus of the blade part 40a is smaller than that of the pinching base plate 30a, and a Young's modulus of the blade part 40b is smaller than that of the pinching base plate 30b. The blade part 40 directly holds the clip 100. Since the blade part 40 has a small Young's modulus, the blade part 40 is easy to be elastically deformed by a tensile load. This enables easy release of the clip 100 from the pinching part 20 of the clip device 10.

Since the pinching base plate 30a has a Young's modulus greater than the Young's modulus of the blade part 40a and the pinching base plate 30b has a Young's modulus greater than the Young's modulus of the blade part 40b, the pinching base plates 30a and 30b are hard to be elastically deformed by a tensile load. The pinching base plates 30a and 30b of the pinching part 20 are thus hard to be deformed in the axial direction. This keeps the holding position of the pinching part 20 in the axial direction even if the attachment and removal of the clip 100 is repeated with the clip device 10.

The Young's modulus is calculated using unloading curves obtained by nanoindentation in accordance with ISO14577. Nanoindentation is an indentation hardness test method. In the method, a diamond indenter is pressed against a test piece with a load. P (N), and the depth h (m) of the entry of the indenter in the test piece is measured with a vertical displacement meter. The composite Young's modulus Er of the test sample and the indenter is calculated by formula 1 using the inclination of an unloading curve (P-h curve) at the maximum load Pmax. The unloading curve is obtained by sequentially measuring the indentation depths from the beginning of loading to the end of the loading. In formula 1, A is a contact area of an indenter with a test piece during loading, and ß is a constant determined by the shape of the indenter. In the case of a triangular pyramid indenter such as a Berkovich, which is generally used as a nanoindenter, ß=1.034.

$$E_r = \frac{\sqrt{\pi}}{2\beta\sqrt{A}\left[\frac{dh}{dP}\right]_{Pmax}}$$ (Formula 1)

The composite Young's modulus Er is expressed in formula 2 using the Young's modulus Es of a test sample, the Young's modulus Ei of an indenter, the Poisson's ratio vs of the test sample, and the Poisson's ratio vi of the indenter. The Young's modulus Es of the test sample is calculated using formula 1 and formula 2.

$$E_r = \left[\frac{(1-v_s^2)}{E_s} + \frac{(1-v_i^2)}{E_i}\right]^{-1}$$ (Formula 2)

To achieve easy release of the clip 100 from the clip device 10, it is also important to form the blade part 40 so that the blade part 40 is easy to be elastically deformed by a reduced tensile load. In the clip device 10 of the present invention, the blade part 40 has a width smaller than the width, of the pinching base plate 30. In the clip device 10 of FIG. 1, the blade part 40 has a width not more than half of the width of the pinching base plate 30.

The blade part 40 is formed toward an inside of the pinching base plate 30 for holding the clip 100. The angle θ between the blade part 40 and the pinching part 30 in preferably an obtuse angle. The angle θ between the blade part 40 and the pinching base plate 30 is preferably larger than 90° and smaller than 180°. This ensures the holding of the clip 100. The upper limit of the range of the angle θ between the blade part 40 and the pinching base plate 30 is more preferably 150° or fewer, and much more preferably 130° or lower. The lower limit of the range of the angle θ between the blade part 40 and the pinching base plate 30 is more preferably 100° or higher, and much more preferably 110° or higher.

The pinching base plate 80 and the blade part 40 are preferably integrally formed, "integrally formed" means that the blade part 40a is formed on the distal side of the pinching base plate 80a and the blade part 40b is formed on the distal side of the pinching base plate 30b by bending a single member at desired positions as in the two pinching base plates 30a and 80b are formed. This eliminates the necessity for joining the pinching base plates 30a and 30b by mechanical securing such as using screws or caulking, welding, or bonding, which simplifies the manufacturing process of the pinching part 20. Mechanical securing, welding, or bonding is possible, however stress concentration may occur in boundary of joining different members, so that the integral forming is preferable for the purpose of repeated usage.

FIGS. 4A to 4D are plan views of the clip device 10 seen from the axial direction, and they show examples of a shape of the blade parts 40. As shown in FIG. 4A, it is preferred that a width of the blade part 40a is the almost same width as the base plate 30a, a width of the blade part 40b is the almost same width as the base plate 30b, and each length of two of the blade parts 40a and 40b is not more than half of an inner diameter of the inner tubular body 80. Since the pinching base plate 30 has the almost same width as the width of the blade part 40, the manufacturing process is easy. Since the blade part 40 has a length not more than half of the inner diameter of the inner tubular body 80, the tensile load to be applied to the blade part 40 can be reduced.

As shown in FIG. 4B, it is preferred that the width of the blade part 40a is smaller than the width of the base plate 30a, the width of the blade part 40b is smaller than the width of the base plate 30b, and each length of two of the blade parts 40a and 40b is not more than half of the inner diameter of the inner tubular body 80. Since the two blade parts 40a and 40b respectively have a width smaller than the width of the pinching base plates 30a and 30b and the blade part 40 has a length not more than half of the inner diameter of the inner tubular body 80, the tensile load to be applied to the blade part 40 can be reduced.

As shown in FIG. 4C, it is also preferred that the width of the blade part 40*a* is smaller than the width of the base plate 80*a*, the width of the blade part 40*b* is smaller than that of the base plate 30*b*, and each length of two of the blade parts 40*a* and 40*b* is not less than half of the inner diameter of the inner tubular body 80. Since two of the blade parts 40*a* and 40*b* respectively have a width smaller than the width of the pinching base plates 30*a* and 30*b*, the tensile load to be applied to the blade part 40 can be reduced. Since the blade part 40 is long, the holding position of the pinching part 20 can easily be confirmed.

As shown in FIG. 4D, the blade part 40*a* provided on a tip of one of the pinching base plate 30*a* and the blade part 40*b* provided on a tip of the other of the pinching base plate 30*b* are preferably alternately arranged. "Alternately arranged" means that the blade parts 40*a* and 40*b* provided on each tip of the two pinching base plates 30*a* and 30*b* are alternately arranged with each other in the width direction of the blade parts 40*a* and 40*b*. The alternate arrangement of the blade parts 40*a* and 40*b* enables the pinching part 20 to easily continue to hold the clip 100, which prevents the clip 100 from falling off the clip device 10 for an endoscope.

As shown in FIG. 4O, it may be acceptable that the blade part 40*a* has a cutout 43*a* and the blade part 40*b* has a cutout 43*b*, to enable easy holding of the clip 100 with the pinching part 20.

A thickness of the blade part 40 is preferably smaller than that of the pinching base plate 30. Since the smaller thickness makes the blade part 40 easier to be elastically deformed, the tensile load to be applied to the blade part 40 can be reduced.

The blade part 40 is preferably composed of an elastic material, more preferably composed of a Ni—Ti alloy. A Ni—Ti alley has not only excellent strength, biocompatibility and corrosion resistance, but also super elasticity and excellent shape recovery properties. The blade part 40 thus easily recovers the original shape even if the attachment and removal, of the clip 100 are repeated. The blade part 40 is also preferably composed of a stainless steel. A stainless steels also has excellent biocompatibility and corrosion resistance. If the blade part 40 is composed of a Ni—Ti alloy or a stainless steel containing one or more of Co, V and Cr in 1% to 5%, the blade part 40 will become easier to be elastically deformed with a smaller Young's modulus.

The present invention includes the clip device 10 for an endoscope further comprising a first handle 90 connected to a proximal side of the inner tubular body 80 and being movable in the axial direction with respect to the outer tubular body 70, and a second handle 91 connected to a proximal side of the line member 50 and being movable in the axial direction with respect to the outer tubular body 70.

FIG. 5 is a plan view of a proximal side of the clip device 10 for an endoscope according the embodiment. As shown in FIG. 5, the first handle 90 is closer to the proximal side than the second handle 91. As the first handle 90 is moved toward the proximal side with respect to the outer tubular body 70, the inner tubular body 80 is moved together toward the proximal side. As the second handle 91 is moved toward the proximal side with respect to the enter tubular body 70, the line member 50 and the pinching part 20 are moved together toward the proximal side. These first handle 90 and second handle 91 facilitate the moving operation of the inner tubular body 80 and the line member 50.

As shown in FIG. 5 the first handle 90 and the second handle 91 are preferably connected with each other by an elastic member 93. As the second handle 91 is moved toward the proximal side, a coil spring as the elastic member 93 is contracted toward the proximal side while accumulating elastic energy so that the restoring force of the coil spring can be used for moving back the second handle 91 toward the distal side.

As shown in FIG. 5, a holding member 95 may be disposed outside of the proximal side of the outer tubular body 70 for facilitating the insertion of the inner tubular body 80 into the outer tabular body 70. The holding member 95 may have an opening 97 extending from the outer surface for injecting liquid into the inner tubular body 80.

FIG. 6 is a perspective view of an indwelling clip 100 comprising two of arm parts 120*a* and 120*b*, a tip part 123*a* formed toward an inside (Y direction in FIG. 6) of the arm part 120*a*, and a tip part 123*b* formed toward an inside (the Y direction in FIG. 6) of the arm part 120*b*. The clip 100 is operated by controlling the opening and closing of the arm parts 120*a* and 120*b* to pinch a target site such as a lesion with the tip parts 123*a* and 123*b*. In FIG. 6, the arm part 120*a* has an opening 125*a* on distal side and the arm part 120*b* has an opening 125*b* on distal side, which makes the clip 100 easy to be deformed to pinch a target site during operation.

In FIG. 6, the tip part 123*a* of the clip 100 has the almost same width as the width of the distal end 122*a* of the arm part 120*a*, and the tip part 128*b* of the clip 100 has the almost same width as the width of the distal end 122*b* of the arm part 130*b*. Alternatively, the clip having a cutout in the tip parts 123*a* and 123*b*, or the clip including the tip part 123*a* having a width smaller than the width of the distal end 122*a* of the arm part 120*a* and the tip part 123*b* having a width smaller than the width of the distal end 122*b* of the arm part 120*b*, can be also preferably used.

The clip 100 is provided with a fastener member 110 having an outer diameter larger than the inner diameter of the inner tubular body 80 and being movable in the axial direction. The fastener member 110 is disposed around the clip 100 for controlling the opening and closing of the clip 100. The fastener member 110 may have a circular cylindrical, shape or a polygonal cylindrical shape. The proximal side of the clip 100 is held by the pinching part 20 of the clip device 10. The fastener member 110 has an outer diameter larger than the inner diameter of the inner tubular body 80 accommodating the pinching part 20. When the pinching part 20 is pulled toward the proximal side, the proximal end of the fastener member 110 comes into contact with the distal end of the inner tabular body 80, which prevents the clip 100 from being pulled into the inner tubular body 80. If the clip 100 is pulled into the inner tubular body 80, the clip 100 cannot be placed in a body, which makes it difficult to smoothly perform the operation.

2. Method for Installing Indwelling Clip

A method for installing a clip 100 used the clip device 10 will be described in detail with reference to FIGS. 7 to 11. The clip device 10 used in the present explanation comprises the enter tubular body 70, the inner tubular body 80, the line member 50 and the pinching part 20, wherein the pinching part 20 has two pinching base plates 30*a* and 30*b* be adjacent to each other in the proximal side, the blade part 40*a* is provided at a distal end of the pinching base plate 30*a*, and the blade part 40*b* is provided at a distal end of the pinching base plate 30*b*. A width of the blade part 40*a* is smaller than that of the pinching base plate 30*a*, a width of the blade part 40*b* is smaller than that of the pinching base plate 80*b*, a Young's modulus of the blade part 40*a* is smaller than that of the pinching base plate 30*a*, and a Young's modulus of the blade part 40*b* is smaller than that of the pinching base plate 30*b*. The clip 100 further comprises arm parts 120*a* and 120*b*, a tip part 123*a* formed toward an inside of the arm part 120*a*, and a tip part 123*b* formed toward an inside of the arm part 120*b*, and a fastener member 110 is provided in an outer side of the clip 100.

(Step 1) Alignment of Clip Device with Clip

The clip device 10 is aligned with the clip 100. As shown in FIG. 7, the distal end of the pinching part 20 is exposed out of the inner tubular body 80 of the clip device 10 by pushing the second handle 91 toward the distal side. Specifically as the line member 50 and the pinching part 20 are moved toward the distal side, the pinching base plate 80*a* with the blade part 40*a* and the pinching base plate 30*b* with the blade part 40*b* are released from the inward pressing force (in the X direction in FIG. 8) applied by the inner side of the inner tubular body 80 to separate from each other in the outward direction, which gradually opens the pinching part 20.

When the distance between the distal ends 41*a* and 41*b* of the two blade parts 40*a* and 40*b* becomes greater than the proximal width of the clip 100 and the pinching part 20 opens widely enough, the blade parts 40*a* and 40*b* are aligned with the proximal end 126 of the indwelling clip 100 in the axial direction. The fastener member 110 of the clip 100 is disposed on the proximal side.

(Step 2) Holding Clip with Clip Device

The second handle 91 is then pulled toward the proximal side to pull the pinching part 20 into the inner tubular body 80. When the pinching part 20 is open, the proximal edges of the pinching base plates 30*a* and 30*b* are in contact with the inner wall of the inner tubular body 80. When the pinching part 20 is pulled toward the proximal side together with the line member 50, the distal edges of the pinching base plates 30*a* and 30*b* come into contact with the inner tubular body 80. As the portions of the pinching part 20 outside of the inner tubular body 80 become narrower, the blade parts 40*a* and 40*b* get closer to each other until the blade parts 40*a* and 40*b* hold the indwelling clip 100. To prevent the clip 100 from being completely closed before being placed in a body, pulling the pinching part 20 into the inner tubular body 80 should be stopped when the distal side of the indwelling clip 100 reaches the inner tubular body 80.

When the clip device 10 with the clip 100 is inserted into the forceps channel of an endoscope, the inner tubular body 80 and the clip 100 are inserted into the outer tubular body 70 not to damage the forceps channels. As shown in FIG. 8, the first handle 90 and the second handle 91 are moved together toward the distal side with respect to the outer tubular body 70 until the outer tubular body 70 covers the clip 100. As the clip 100 gradually enters the outer tubular body 70, the arm 120*a* with the tip part 123*a* and the arm 120*b* with the tip part 123*b* of the clip 100 get closer to each other as in the pinching part 20.

(Step 3) Holding Target Site

The endoscope accommodating the clip device 10 including the outer tubular body 70 disposed the clip 100 and the inner tubular body 80 inside is inserted from the side of the forceps opening until the distal end of the outer tubular body 70 reaches the area near a lesion of a patient. At this time, the operator axially rotates the first handle 90 and the second handle 91 to adjust the orientation of the tip parts 123*a* and 123*b* of the clip 100 with respect to the lesion for holding the lesion, while confirming the position and condition of the lesion on the image obtained from the endoscope. As shown in FIG. 9, when the first handle 90 and the second handle 91 are pushed together toward the distal side with respect to the outer tubular body 70, a part of the clip 100 comes out of the outer tubular body 70 while the pinching part 20 remains in the inner tubular body 80. As the arm parts 120*a* and 120*b* of the clip 100 come out of the outer tubular body 70 while being released from the inner shape of the outer tubular body 70, the clip 100 gradually opens.

As shown in FIG. 10, the second handle 91 is moved toward the proximal side with respect to the first handle 90 to pull the line member 50 toward the proximal side for holding the lesion with the clip 100. While the clip 100 gradually closes, the clip 100 is palled into the inner tubular body 80 from its proximal end. Since the fastener member 110 around the clip 100 has an outer diameter larger than the inner diameter of the inner tubular body 80, the fastener member 110 is not pulled into the inner tubular body 80. Since the fastener member 110 is caught on the clip 100 at the outer position with the greatest distance between the arm parts 120*a* and 120*b*, the clip 100 is fastened by the fastener member 110 while holding the lesion.

(Step 4) Release of Indwelling Clip from Pinching Part

The clip 100 is then released from the clip device 10 to be placed in a body. The second handle 91 is moved toward the proximal side with respect to the outer tubular body 70 to pull the pinching part 20 of the clip device 10 toward the proximal side. This applies a tensile load to the blade parts 40*a* and 40*b* and the blade parts 40*a* and 40*b* expand outward with an increasing angle θ between the pinching base plate 30*a* and the blade part 40*a* and between the pinching base plate 30*b* and the blade part 40*b*. As shown in FIG. 11, the clip 100 held by the pinching part 20 of the clip device 10 rides over the blade parts 40*a* and 40*b* to be released from the clip device 10. In the present invention, the method for installing the indwelling clip 100 does not involve pushing the pinching part 20 toward the distal end side with respect to the inner tubular body 80 for placing the clip 100 in a body after holding a target site such as a lesion with the clip 100. In the method, the clip 100 can easily be released from the clip device 10 only by pulling the pinching part 20 toward the proximal end side after holding the target site with the clip 100. Since the blade part 40 of the clip device 10 of the present invention has a width smaller than the base plate 30 and also has a Young's modulus smaller than the base plate 30, the blade part is easy to be elastically deformed.

This application claims the benefit of the priority date of Japanese patent application No. 2014-217255 filed on Oct. 24, 2014. All of the contents of the Japanese patent application No. 2014-217255 filed on Oct. 24, 2014, are incorporated by reference herein.

REFERENCE SIGNS LIST

10: a clip device for an endoscope
20: a pinching part
30, 30*a*, 30*b*: a pinching base plate
40, 40*a*, 40*b*: a blade part
50: a line member
70: an outer tubular body
80: an inner tubular body
90: a first handle
91: a second handle
100: an indwelling clip
110: a fastener member

The invention claimed is:
1. A clip device for an endoscope comprising:
an outer tubular body;
an inner tubular body provided in the outer tubular body;
a line member placed in the inner tubular body;

a pinching part for holding an indwelling clip, a proximal end of the pinching part connected to a distal side of the line member; and an indwelling clip for holding a target site, the indwelling clip held by the pinching part, wherein the pinching part has two pinching base plates, each of the two pinching base plates has a blade at a distal end, each of said blades extending toward an inside of the respective pinching base plate, so that the indwelling clip is held by the blades of the pinching part, a Young's modulus of the blades is smaller than that of the pinching base plates, each of the pinching base plates has a principal surface extending from the proximal end toward each of the blades in a longitudinal direction and having a width in a direction perpendicular to the longitudinal direction, and a width of each of the blades is smaller than the width of the pinching base plates in the wide direction perpendicular to the longitudinal direction.

2. The clip device for an endoscope according to claim 1, wherein the blade provided on a tip of one of the pinching base plate and the blade provided on a tip of the other pinching base plate are alternately arranged.

3. The clip device for an endoscope according to claim 1, wherein for each of the pinching base plates, an angle between the pinching base plate and the blade at the distal end of the pinching base plate is larger than 90° and smaller than 180°.

4. The clip device for an endoscope according to claim 1, wherein for each of the pinching base plates, the pinching base plate and the blade at the distal end of the pinching base plate are integrally formed.

5. The clip device for an endoscope according to claim 1, wherein the blades are composed of a Ni—Ti ahoy or a stainless steel.

6. The clip device for an endoscope according to claim 1, further comprising a first handle connected to a proximal side of the inner tubular body and being movable in the axial direction with respect to the outer tubular body, and a second handle connected to a proximal side of the line member and being movable in the axial direction with respect to the outer tubular body.

7. The clip device for an endoscope according to claim 1, wherein a length of each of the blades is not more than half of an inner diameter of the inner tubular body.

8. The clip device for an endoscope according to claim 1, wherein a thickness of each of the blades is smaller than that of each of the pinching base plates.

9. The clip device for an endoscope according to claim 1, wherein each of the pinching base plates has a curved part which is curved toward an inside of the pinching part in at least a part of the pinching base plates.

10. The clip device for an endoscope according to claim 1, wherein each of the blades is composed of a material different from a material of each of the pinching base plates.

* * * * *